(12) United States Patent  (10) Patent No.: US 7,833,273 B2
Buettner-Janz et al.  (45) Date of Patent: Nov. 16, 2010

(54) PHYSIOLOGICALLY MOVABLE INTERVERTEBRAL DISC PROSTHESIS FOR THE LUMBAR AND CERVICAL SPINE

(76) Inventors: Karin Buettner-Janz, Möllhausenufer 27, Berlin (DE) 12557; Eiko Büttner, Simon-Dach-Str. 28-29, Berlin (DE) 10245

( * ) Notice: Subject to any disclaimer, the term of this patent is extended or adjusted under 35 U.S.C. 154(b) by 216 days.

(21) Appl. No.: 11/379,080

(22) Filed: Apr. 18, 2006

(65) Prior Publication Data
US 2006/0241772 A1 Oct. 26, 2006

Related U.S. Application Data

(63) Continuation-in-part of application No. PCT/DE2005/001884, filed on Oct. 18, 2005.

(30) Foreign Application Priority Data
Oct. 18, 2004 (WO) .............. PCT/DE2004/002331

(51) Int. Cl.
*A61F 2/44* (2006.01)
(52) U.S. Cl. .............. 623/17.14; 623/17.15; 623/17.16; 606/246; 606/249
(58) Field of Classification Search ... 623/17.11–17.16; 606/61, 246–279
See application file for complete search history.

(56) References Cited

U.S. PATENT DOCUMENTS

| 4,997,432 | A | * | 3/1991 | Keller .................... 623/17.11 |
| 5,258,031 | A | | 11/1993 | Salib et al. |
| 5,401,269 | A | * | 3/1995 | Buttner-Janz et al. .... 623/17.15 |
| 5,562,738 | A | * | 10/1996 | Boyd et al. ............... 623/17.15 |
| 5,888,226 | A | * | 3/1999 | Rogozinski ............... 623/17.16 |
| 6,478,822 | B1 | * | 11/2002 | Leroux et al. ............ 623/17.14 |
| 7,204,852 | B2 | * | 4/2007 | Marnay et al. ........... 623/17.16 |
| 2003/0074069 | A1 | * | 4/2003 | Errico et al. ............. 623/17.14 |
| 2003/0139813 | A1 | * | 7/2003 | Messerli et al. .......... 623/17.11 |
| 2003/0191534 | A1 | * | 10/2003 | Viart et al. ............... 623/17.15 |

(Continued)

FOREIGN PATENT DOCUMENTS

EP  0 560141  9/1993

(Continued)

OTHER PUBLICATIONS

Bomley, Anna, Spinal Devices: Market opportunity and technology trends. Clinica Reports, Jun. 2004, PJB Publications, Ltd., Surrey, United Kingdom.

*Primary Examiner*—Eduardo C Robert
*Assistant Examiner*—Jan Christopher Merene
(74) *Attorney, Agent, or Firm*—Joyce von Natzmer; Pequignot + Myers LLC

(57) ABSTRACT

Disclosed is an intervertebral disc prosthesis for the total replacement of a natural intervertebral disc within the lumbar and cervical spine, comprising of articulating sliding partners. The upper sliding partner has means for a firm assembly to an upper vertebral body and the lower sliding partner has means for a firm assembly to a lower vertebral body. At least one sliding surface is between two sliding partners. Two- and three-part functional designs are planned and both having in common, that, as a result of the shape of the articulating surface(s), the laterolateral and dorsoventral motion amplitudes differ. The resulting angles including the rotation around a fictitious vertical axis can be defined to a desired extent.

33 Claims, 11 Drawing Sheets

U.S. PATENT DOCUMENTS

| | | |
|---|---|---|
| 2003/0208273 A1 | 11/2003 | Eisermann et al. |
| 2004/0117021 A1* | 6/2004 | Biedermann et al. ...... 623/17.15 |
| 2004/0117022 A1* | 6/2004 | Marnay et al. ............ 623/17.16 |
| 2004/0143332 A1* | 7/2004 | Krueger et al. ............ 623/17.14 |
| 2004/0158328 A1 | 8/2004 | Eisermann |
| 2005/0165486 A1* | 7/2005 | Trieu ........................ 623/17.13 |
| 2005/0261772 A1* | 11/2005 | Filippi et al. .............. 623/17.13 |
| 2006/0235527 A1 | 10/2006 | Buettner-Janz et al. |
| 2006/0235528 A1 | 10/2006 | Buettner-Janz |
| 2006/0235531 A1 | 10/2006 | Buettner-Janz |
| 2007/0100454 A1* | 5/2007 | Burgess et al. ............ 623/17.14 |
| 2007/0173942 A1* | 7/2007 | Heinz et al. ............... 623/17.15 |
| 2007/0299524 A1* | 12/2007 | Rivin ........................ 623/17.13 |
| 2008/0133013 A1* | 6/2008 | Duggal et al. ............. 623/17.16 |

FOREIGN PATENT DOCUMENTS

| | | |
|---|---|---|
| EP | 1188423 A1 | 3/2002 |
| WO | WO 00/53127 | 9/2000 |
| WO | WO 2004/064692 | 8/2004 |
| WO | PCT/DE2005/001884 | 1/2006 |

\* cited by examiner

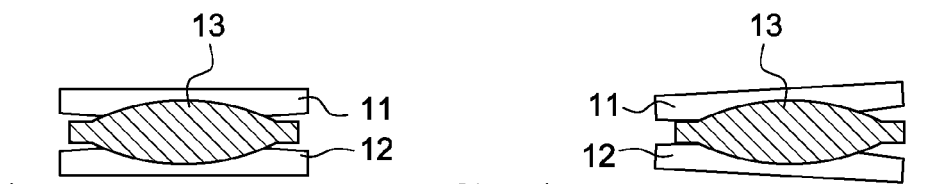
*FIG. 5a*
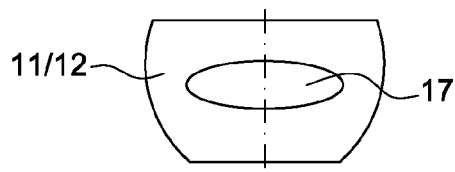
*FIG. 5b*
*FIG. 5c*
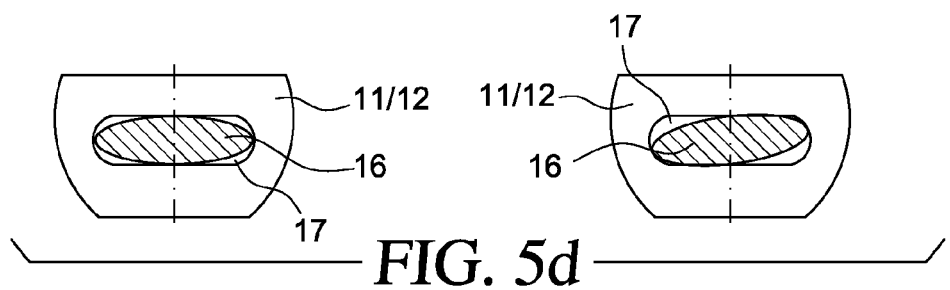
*FIG. 5d*
*FIG. 5e*
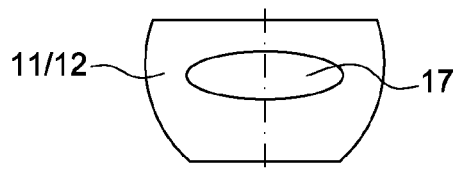
*FIG. 5f*
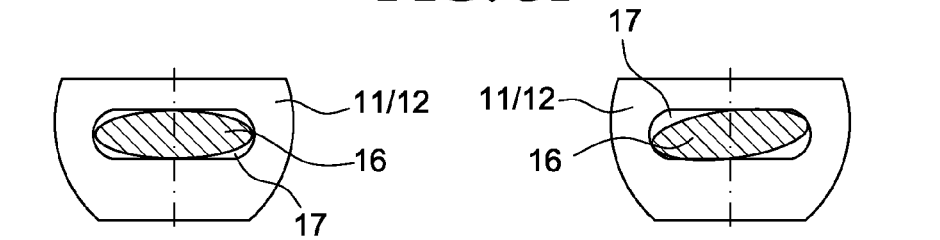
*FIG. 5g*

PHYSIOLOGICALLY MOVABLE INTERVERTEBRAL DISC PROSTHESIS FOR THE LUMBAR AND CERVICAL SPINE

CROSS REFERENCE SECTION

This is a continuation-in-part application of international application no. PCT/DE2005/001884, filed Oct. 18, 2005 designating the U.S. and claiming priority from international application no. PCT/DE2004/002331, filed Oct. 18, 2004. Both of these applications are incorporated herein by reference in their entirety.

FIELD OF THE INVENTION

The invention relates to an intervertebral disc prosthesis for the total replacement of an intervertebral disc of the lumbar and cervical spine.

BACKGROUND OF THE INVENTION

The idea of function-retaining artificial replacements for intervertebral discs is younger than that for replacements of artificial joints of extremities, but nonetheless about 50 years old [Büttner-Janz, Hochschuler, McAfee (Eds.): The Artificial Disc. Springer Verlag, Berlin, Heidelberg, N.Y. 2003]. It is a response to biomechanical considerations, unsatisfactory results of fusion surgeries, disorders adjacent to fusion segments and the development of new materials with greater longevity.

The publications and other materials, including patents, used herein to illustrate the invention and, in particular, to provide additional details respecting the practice are incorporated herein by reference.

By means of function-retaining disc implants it is possible to avoid fusion surgery, i.e. to maintain, or to restore the mobility within the intervertebral disc space. In an in-vitro experiment it is also possible to achieve a normalization of the biomechanical properties of the motion segment to a large extent through the implantation of an artificial intervertebral disc after a nucleotomy.

Implants for the replacement of the whole intervertebral disc differ from those for the replacement of the nucleus pulposus. Accordingly, implants for the total replacement of the intervertebral disc are voluminous; they are implanted via a ventral approach. An implantation of a prosthesis for total replacement of the intervertebral disc immediately after a standard nucleotomy can therefore not be carried out.

The indication for a function-retaining intervertebral disc replacement as an alternative to the surgical fusion includes, besides the painful discopathy, also pre-operated patients with a so-called post discectomy syndrome, patients with a recurrent herniated intervertebral disc within the same segment and patients having a pathology within the neighboring intervertebral disc as a consequence of fusion surgery.

Presently, a total of more than 10 different prostheses are clinically used for the total replacement of intervertebral discs. For the lumbar spine the CHARITÉ Artificial Disc, the PRODISC, the MAVERICK, the FLEXICORE and the MOBIDISC (Overview in Clinica Reports, PJB Publications Ltd., June 2004) are particularly well known, and for the cervical spine the Bryan prosthesis, the Prestige LP prosthesis, the PRODISC-C and the PCM prosthesis, which will be described below.

Following its further development to PRODISC II, the PRODISC prosthesis has been in use as a lumbar spine implant since 1999. Although with respect to its components (a three-part intervertebral disc prosthesis), it is functionally a two-part prosthesis with its sliding partners made of metal and polyethylene. Implantations of the PRODISC are carried out in the lumbar spine and with an adapted model of the prosthesis, the PRODISC-C, also in the cervical spine. Different sizes, heights (achieved by the polyethylene core) and angles of lordosis (achieved by the metal endplates) are available. Bending forward and backward as well as to the right and to the left is possible to the same extent of motion; the axial rotation is not limited in the construction.

The same applies to both two-part prostheses for the cervical spine, the PCM prosthesis with its sliding partners metal and polyethylene and the PRESTIGE LP prosthesis with its sliding partners metal-metal. As special feature of the construction of the PRESTIGE LP prosthesis it has the possibility for an anterior-posterior translation, due to the horizontal ventrally prolonged concavity, which, in a frontal section, has the same radius as the convexity.

The MAVERICK and the FLEXICORE for the lumbar spine are functionally a two-part prostheses with spherical convex-concave sliding partners, both with sliding partners made of metal. In contrast, the MOBIDISC is functionally a three-part prosthesis with sliding partners of metal-polyethylene and two articulation surfaces. One area is a segment of a sphere, as it is in the three afore mentioned prostheses, with a convex and a concave surface of the articulating partners each of the same radius, the other area of the MOBIDISC being plane. Although a limitation of the axial rotation is planned within the plane section, it is not limited within the convex-concave area of articulation. In contrast the FLEXICORE has a small stopping area within the spherical sliding surfaces limiting the rotation movement.

The BRYAN prosthesis is clinically used as a compact prosthesis for total replacement of intervertebral discs of the cervical spine. It is attached to the vertebral bodies by convex titanium plates with a porous surface and achieves its biomechanical properties by virtue of a polyurethane nucleus.

The longest experience exists with the CHARITÉ prosthesis, which is the subject matter of DE 35 29 761 C2 and U.S. Pat. No. 5,401,269 specifications. This prosthesis was developed in 1982 by Dr. Schellnack and Dr. Büttner-Janz at the Charité in Berlin and was later on named SB CHARITÉ prosthesis. In 1984 the first surgery took place. The intervertebral disc prosthesis was further developed into model III and has been implanted over 10,000 times worldwide (DE 35 29 761 C2, U.S. Pat. No. 5,401,269) since 1987 and is still being used. The prosthesis is functionally three-parted with the sliding partners being metal and polyethylene with two identical spherical sliding surfaces. On the one hand it has a transversally mobile polyethylene core and on the other hand the accordingly adapted concave cups within two metal endplates. For the adaptation to the intervertebral space, the CHARITÉ prosthesis provides different sizes of metal plates and different heights of size adapted sliding cores as well as angled prosthetic endplates, which when implanted vice versa in sagittal direction can also be used as replacement for the vertebral body. The primary fixation of the CHARITÉ prosthesis is achieved by six teeth, which are located in groups of three slightly towards the middle next to the frontal and rear edge of each prosthetic plate.

The other prosthesis have other primary fixations on their surfaces directed towards the intervertebral bodies, e.g. a sagitally running keel, a structured surface, a convex shape with for instance crosswise running grooves and combinations thereof, also with differently located teeth. Furthermore screw fixations can be used, either from ventral or from within the intervertebral space into the intervertebral body.

To assure a long-term fixation of the prosthetic endplates to the intervertebral bodies and to thus generate a firm connection with the bone, a surface was created in similitude to cement-free hip and knee prostheses, which combines chrome-cobalt, titanium and calcium phosphate in such a way that it is possible for bone to grow directly onto the endplates. This direct connection between prosthesis and bone, without the development of connective tissue, makes a long-term fixation of the artificial intervertebral disc possible and reduces the danger of loosening or displacements of the prosthesis and material breakage.

One primary objective of function retaining intervertebral disc replacements is to closely adapt the motions of the prosthesis to the ones of a healthy intervertebral disc. Directly connected to this is the motion and stress for the facet joints, which following inappropriate biomechanical stress have their own potential for disorders. There can be abrasion of the facet joints (arthritis, spondylarthritis), with a formation of osteophytes. As result of these osteophytes and also by a pathologic course of motion of the intervertebral disc alone, the irritation of neural structures is possible.

A healthy intervertebral disc is, in its interactions with other elements of the motion segment, composed in such a way that it allows for limited motion. For example, within the intervertebral disc, motions to the front and back are combined with rotary motions, and side motions are also combined with other motions. The motion amplitudes of a healthy intervertebral disc are very different, with respect to the extension (bending back) and flexion (bending forward) as well as to the lateral bending (right and left) and rotary motion. Although of common basic characteristics, there are differences between the motion amplitudes of the lumbar and cervical spine.

During motion of the intervertebral disc the centre of rotation changes, i.e. the motion of the intervertebral disc does not take place around a fixed center. Due to a simultaneous translation movement of the adjacent vertebrae, the center changes its position constantly (inconstant center of rotation). The prosthesis according to DE 35 29 761 C2 shows a construction which differs relative to other available types of prostheses which are build like a ball and socket joint, and as a result move around a defined localized centre of rotation. By virtue of the three-part assembly of the prosthesis according to DE 35 29 761 C2, with two metallic endplates and the interpositioned freely mobile polyethylene sliding core, the course of motion of a healthy intervertebral disc of the human spine is mimicked as far as possible, however without the exact motion amplitudes in the specific motion directions.

A further important feature of the healthy lumbar intervertebral disc is its trapezium shape, which is primarily responsible for the lordosis of the lumbar and cervical spine. The vertebral bodies themselves contribute only to a minor extent to the lordosis. During prosthetic replacement of intervertebral discs the lordosis should be maintained or reconstructed. The Charité disc prosthesis provides four differently angled endplates, which moreover can be combined with each other. However, this surgery requires more surgical effort and has the risk of damaging the vertebral endplates which is associated with a danger of subsidence of the prosthesis into the vertebral bodies. Additionally, if the adjustment of the lordosis is poor and an optimal load of the center of the polyethylene core was not achieved, the prosthesis has to be removed completely.

To avoid sliding or a slip-out of the middle sliding partner from the endplates, DE 35 29 761 C2 discloses a sliding core with a two-sided partly spherical surface (lenticular), with a plane leading margin and, at the exterior, with a ring bulge, which will lock between the form-adapted endplates during extreme motion. DE 102 42 329 A1 discloses a similar intervertebral disc prosthesis which has a groove around the contact surfaces, in which an elastic ring is embedded that is in contact with the opposite contact area to improved guidance. EP 0 560 141 B1 describes a three-part intervertebral disc prosthesis, which also consists of two endplates and an interpositioned prosthetic core. The intervertebral disc prosthesis, described in this document, provides resistance during rotation of its endplates in opposing directions around a vertical rotary axis without a contact between the prosthetic endplates. This is achieved by a soft limitation of the endplates during rotation onto the prosthesis core caused by the weight, which acts on the plates as a result of the biomechanical load transfer within the spine, because the corresponding radii of curvature differ in a median-sagittal and frontal transection.

The above mentioned models are permanently anchored in the intervertebral spaces as implants. Especially due to a load transfer over too small surface areas, a migration of the endplates into the vertebral bodies and thus a dislocation of the complete implant is possible in middle to long-term, resulting in artificial stress for the vertebral bodies and the adjacent nerves and in the end for the total motion segment, and leading to new complaints of the patients. The long-term stability of the polyethylene and the restricted mobility of the intervertebral disc prosthesis due to an inappropriate load on the polyethylene within the intervertebral space have to be discussed. Insufficiently adapted ranges of motion and adverse biomechanical stress in the motion segment can possibly lead to persistence of the complaints or later on to new complaints of the patients.

U.S. Pat. No. 6,706,068 B2 on the other hand, describes an intervertebral disc prosthesis comprising an upper and lower part, in which the parts are built correspondingly towards each other. No intermediate part as middle sliding partner exists. Different designs are realized for the interdigitating and articulating partners, resulting in a two-part prosthesis. The design is however limited to structures having either edges or corners so that both parts of the prosthesis articulate with each other; in this case it is not possible to speak of sliding partners. Furthermore two sliding partners are described having one convex part towards the interior of the prosthesis and the other sliding partner is correspondingly shaped concavely. This kind of prosthesis, however, allows restricted movements of the artificial intervertebral disc only. The concave protuberance corresponds to a part of a ball with the according radius. U.S. Pat. No. 6,706,068 B2 further shows a two-part disc prosthesis having convex and concave partial areas on each sliding partner corresponding to concave and convex partial areas of the other sliding partner. According to the disclosure of U.S. Pat. No. 6,706,068 B2 several fixed points of rotation are generated.

The U.S. Pat. No. 5,258,031 discloses a two-part disc prosthesis, in which the two endplates articulate with each other by a ball and socket joint. The joint is located centrally in the frontal section. In a lateral view, the small area of articulation is positioned outside the middle. The articulation areas are spherical in a sagittal view and plane in a frontal view, at the end's small and partly spherical parts are followed by plane skewed ones; these parts have no contact when the other parts of the joint are in contact. Bending to one side with a prosthesis according to the U.S. Pat. No. 5,258,031 is achieved by use of the partly spherical margin of the articulation areas. Whether the lateral inner parts of the endplates come into contact with each other cannot be clearly discerned from the U.S. Pat. No. 5,258,031. At least during one lateral motion, the laterally outwardly opened areas in the bilateral part of the articulation areas do not come into contact. Therefore during lateral bending of the endplates according to the U.S. Pat. No. 5,258,031 the pressure is partly on the spherical margins of the articulation areas only. Because of the pressure distribution only onto points or small areas during side bending, the outer parts of the convex/concave parts are exposed to greater abrasion. The margins of the prosthesis also do not have contact over a large area during the different movements. If the prosthesis according to the U.S. Pat. No. 5,258,031 provides rotation around a vertical axis there is only a bilateral punctiform contact area between the upper and lower endplates.

Refer to EP 1 188 423 A1 for the technical background of intervertebral disc prostheses, which describes an arthroplastic device for intervertebral spaces, comprising a ball and socket joint between a first and a second element, for the surgery in a first and a second vertebra of the spine. Furthermore refer to US 2003/0208273 A1, which discloses a two part intervertebral disc prosthesis with a convex/concave articulation area.

Thus, there is a need for an intervertebral disc prosthesis for the total replacement of intervertebral discs, with which the extent of the movement can be specifically adapted to the anatomy and biomechanics of the lumbar and cervical spine, distributing the pressure load at the end of movements onto as large as possible areas of the sliding partners.

This need is addressed by the present invention. The invention comprises two different types of an intervertebral disc prosthesis, namely a functionally two-part and a functionally three-part prosthesis.

SUMMARY OF THE INVENTION

A functional two-part prosthesis is characterized by
a) a first sliding partner built in such a manner, that the opposite side of the side for the assembly with a vertebral body has a convex surface area (convex curving, convex articulation area, convexity), and
   a. the radius of curvature of the convexity
      i. is identical in frontal and transversal view and results from the rotation of the smaller part of a segment of a circle, located between the intersection points of a secant with a circumference, but the secant does not pass through the center of the circle, and the rotation takes place around the part of the secant inside the circumference, and
      ii. corresponds in sagittal view to a segment of a circle, whose radius is the distance between said secant and said circumference from point a) a. i., and
   b. the convexity is enclosed by a margin, and
b) a second sliding partner on the inside is built with a concave articulation area (concavity), and the geometry of the concavity is defined by
   a. having a corresponding recess to the convexity of the first sliding partner, which
   b. is enclosed by a margin, and
c) the margins of both sliding partners
   a. having an outwardly opening angle (aperture angle) in relation to each other, where
   b. the aperture angles differ at least in a central frontal section compared to a central sagittal section by different inclinations of the margins, to allow the maximal possible contact area of the margins at final grade motions of the sliding partners, and
   c. the different inclinations of the edges transit seamlessly, whereas
   d. at equal aperture angles in a vertical section, bilaterally of the articulation areas the inclinations of the edges are equal or different, and
d) the motion angle is greater in a dorsoventral direction than in a laterolateral direction, resulting from the different radii of curvature sagittally to frontal, and
e) the maximal possible motion of the sliding partners towards each other is determined by
   a. radius of curvature and height of the convexity with respect to the respective edge, and
   b. the design of each corresponding concavity, especially the height in relation to the corresponding edge and shape in relation to the corresponding convexity, and
   c. the oblique or horizontal surrounding edges of the convexity and the concavity.

The functional three-part prosthesis is characterized by,
a) a middle sliding partner having a convex curvature (convex curving, convex articulation area, convexity) on the upper and lower surface, and the radius of curvature of the convexity on the upper and lower surface
   a. is identical in frontal and transversal view and results from the rotation of the smaller part of a segment of a circle, located between the intersection points of a secant with a circumference, but the secant does not pass through the center of the circle, and the rotation takes place around the part of the secant inside the circumference, and
   b. corresponds in sagittal view to a segment of a circle, whose radius is the distance between the secant and the circumference from point a) a. and
b) upper and lower sliding partners are built with concave articulation areas (concavity) on the inside, and the geometry of the concavities of the upper and lower sliding partners is each defined by a corresponding recess to the convexity of the upper and lower side of the middle sliding partner, which is enclosed by a edge, and
c) the edges of the sliding partners have an outwardly opening angle (aperture angle) in relation to each other, where
   a. the aperture angles differ at least in a central frontal section compared to a central sagittal section by different inclinations of the edges, to allow the maximal possible contact area of the edges at final grade motions of the sliding partners, and
   b. the different inclinations of the edges transit seamlessly,
   c. whereas at equal aperture angles in a vertical section, bilaterally of the articulation areas the inclinations of the edges are equal or different, and
d) the motion angle is greater in a dorsoventral direction than in a laterolateral direction, resulting from the different radii of curvature sagittally to frontal, and
e) the maximal possible motion of the sliding partners towards each other is determined by
   a. radius of curvature and height of the convexities, the design of each corresponding concavity, especially the height in relation to the corresponding edge and shape in relation to the corresponding convexity, and
   b. the oblique or horizontal surrounding edges of the convexity and the concavity.

Both prostheses comprise articulation sliding partners of which each upper sliding partner is firmly assembled to an upper vertebral body and each lower sliding partner is firmly assembled to a lower vertebral body and that the sliding partners form interdigitating articulation areas on their inner surfaces that are directed toward each other. Upper and lower sliding partners of a three-part prosthesis as well as both sliding partners of a two-part prosthesis at the same time act as endplates, having means for assembly to an upper or lower vertebral body.

For the narrow anatomical space of the cervical spine both, two- and three-part prosthesis, are intended. The two-part prosthesis can also be of advantage for the lumbar spine in prosthetic implantations in multiple adjacent intervertebral spaces because of its model-immanent stability. The three-part intervertebral disc prosthesis has the advantage that the transversal sliding of two neighboring vertebrae is minimal, resulting in a favorable adaptation to the biomechanics of the motion segment. Furthermore, the three-part prosthesis enables the simulation of an inconstant center of rotation.

With respect to the presented invention, the three body axes are described by the following terms: A "sagittal section" or a view in the "sagittal plane" enables a lateral view, because the section plane runs vertically from the front to the back. The term "front" is synonymous "ventral" and the term "back" to "dorsal". By using these terms, the orientation of the prosthesis within the body is indicated. A "frontal section" or the "frontal plane" is a vertical cross-section from one side to the other. The term "lateral" stands for sidewise. Sagittal and frontal sections are vertical sections as they both run in a vertical plane, but 90 degree displaced from one another. A view in the "transversal plane" or a "transversal section" shows a top-view onto the prosthesis, because it is a horizontal section.

With respect to the description and depiction of the presented invention, an articulation area signifies that region of the sliding partners, which comprises the curved convex and concave parts of the surfaces, which come into contact or articulate with each other. Because of this the term articulation area is synonymous with the term sliding area.

The term "corresponding", with respect to the articulating sliding areas, designates not only congruent convexly and concavely shaped areas articulating with each other—but also designates articulating surfaces that are not completely congruent. Such "deviations" or tolerances regarding the sliding areas of articulating sliding partners can be caused on the one hand by the chosen materials and shapes. On the other hand it may also be intended that the articulating convexity and concavity are not totally congruent, for instance in order to designate the desired possibilities of motion for each the articulating partners directly.

As per the invention, both prostheses have the potential for laterolateral and dorsoventral motion amplitudes that differ in magnitude and the resulting angles including the rotation around a fictitious vertical axis can be defined to their respective extent.

The different lateral and dorsoventral motion angles of an intervertebral disc prosthesis, as per the invention, result from the design of the convex-concave articulation areas and stand in relation to each other, because the radii of curvature, on which they are based, are advantageously defined by a single geometric contiguity according to point a) a. from claim 1 and point a) from claim 2. Thus, the resulting convex surfaces always have a greater radius in a frontal section than in a sagittal section. A complete rotation body according to the features of the independent claims 1 a) a. and 2 a) has— without an edge—the shape of an "American football" or a spindle in which the diameter increases equally continuously from each side to the middle.

Generally speaking, the radii of curvature of the convexity of an intervertebral disc prosthesis, as per the invention, are always smaller in a sagittal section than every radius of curvature in a frontal or transversal section. Lower angles of motion for the lateral movements than for extension/flexion result from this correlation, as is the case with the motion angles in a natural intervertebral disc. Thus the possible angles of motion of an intervertebral disc prosthesis, as per the invention, come close to the ones of a natural intervertebral disc.

A further nonlimiting advantage of an intervertebral disc prosthesis, as per the invention, is that, in certain embodiments, in addition to its approximated angles of motion, which come close to the natural degrees of motion, the rotation is limited softly by a plane contact area. This is in contrast to the so far known intervertebral disc prostheses with either a small or nearly pointed firm stop for the limitation of the rotation, or to intervertebral disc prostheses with convex surfaces derived from a spherical cap with a transition to an, for instance, ellipsoid form, also with a very small plane or pointed limitation of rotation. The design of the convexities and corresponding concavities, as per the invention, assures a protection of the articulating surfaces, because the sliding partners cannot be "twisted" against each other to such an extent that they come in contact by single points only, which would have to bear the whole pressure lasting on the upper and lower sliding partners. Because of this the material or the coating of the sliding partners is less exposed to strain, so that an intervertebral disc prosthesis, as per the invention, is clearly more durable than the prostheses known from the present state of the art.

Besides the advantages resulting from the design of the convex-concave parts of the articulation surfaces as per the invention, the intervertebral disc prostheses may have further advantages. The concavities of upper and lower sliding partner of a two- and three part intervertebral disc prosthesis, as per the invention, are each enclosed by an edge, whereas the convexities of a middle sliding partner of a three-part prosthesis range through the whole upper and lower side i.e. the convexities are without edge, or the convexities are each enclosed by an edge with a similar or different breadth.

An edge, as per the invention, indicates an area located between outer rim of the respective sliding partner and convexity(ies) or concavity(ies). The edges of the respective sliding partners run horizontally and/or at an incline and preferably have a plane surface. It is essential for the design of the surfaces of the edges, that during terminal inclination of the sliding partners towards each other a gap-closure across a maximally possible area between the edges of the sliding partners is achieved. Should the edges not have a plane surface, they have to in any case be designed in such a way that during gap-closure, a maximally possible contact arises between them.

In a preferred version, the heights of the edges in the direct transition area between the articulating surfaces and the area of the edge are differently constructed around the convexity or concavity. The differences in the heights of the edges can on the one hand serve towards the adaptation of the respective maximally possible motions of the sliding partners. On the other hand, partly minimal differences in the height of the edge, for instance dorsoventral to laterolateral, may be caused during production. As per the invention, the height of the edges around convexity(ies) and concavity(ies), particularly in the direct transition area of the articulating area with the area of the edge, may also be equal, so that there are no differences between the arrangement of the respective heights in dorsoventral to laterolateral direction.

The edges of the convexity(ies) and concavity(ies) always have, without incline of the sliding partners toward each other, an outwardly opening angle (aperture angle) in every vertical section plane. The maximal inclination angles are limited by contact of the transition area between concavity(ies) and the area of the edge surrounding the concavity(ies) and the transition area of the corresponding convexity(ies) and, if present, the edge surrounding the convexity(ies). Although this contact is limiting for the further motion of the sliding partners towards each other, it is not the only area outside the concave-convex articulation areas, which come into contact at terminal inclination. The edges of the sliding partners up unto their peripheral rim are designed in such a way, that these also take part at maximum contact. For this purpose the edges have a higher aperture angle ventrally and dorsally than laterally with a smooth transition in the regions of different heights, so that during terminal inclination a gap-closure of the edges is possible. This is because of the greater possibilities for ventral and dorsal inclination and the thus otherwise remaining ventral and dorsal gap during terminal inclination. The closing of the edges is, depending on the direction of motion and direction of the aspect, complete or incomplete.

By this measure, as per the invention, the load bearing area is increased at gap-closure, during which an inclination of the prosthesis up to its limitation takes place. The areas in contact are further protected against abrasion because the pressure is taken up by a plane surface and not by pointed contact areas, resulting in a clearly more durable prosthesis.

Regarding the material of the prosthesis, as per the invention, it is intended, that the sliding partners are constructed as a single piece or at least one sliding partner comprises at least two permanent or firmly, but reversibly attached parts, and the convexity(ies) and/or the concavity(ies) are the parts being permanent or firmly, but reversibly attached to the corresponding sliding partner, or the convexity(ies) and/or concavity(ies) have suitable means for a permanent or firmly, but reversible assembly, wherein parts connected with each other comprise the same or different materials or the surfaces of the parts are coated equally or differently. As suitable means for the assembly, adaptations of the shape of the parts to be connected, as per the invention, are intended, such as recesses or plane broadenings as part of the edge or making up the whole edge. Depending on the chosen design, the respective sliding partners and/or convexity and/or concavity as well as the edge are designated as parts that are to be connected. In the case of a middle sliding partner it is also intended that it results from the assembly of the respective parts.

Where an intervertebral disc prosthesis comprises permanent or firmly, but reversibly attached parts, it is intended that the assembly is achieved by a tongue and groove assembly, a track and corresponding recess, a snap mechanism, by gluing or screwing.

For a three-part intervertebral disc prosthesis, as per the invention, it is intended, that upper and lower sliding partner comprise the same material or are equally coated and the middle sliding partner is made of a different material or is differently coated. It is further intended that all three sliding partners are made of the same material or have the same coating.

The sliding partners are preferably manufactured from well established materials from implantation techniques; for instance upper and lower sliding partner are made of rustproof metal and the middle sliding partner of medicinal polyethylene. Other combinations of materials are also feasible. The use of other alloplastic materials, which may also be bio-active, is intended as well. The sliding partners are preferably high gloss polished at their communicating contact areas to minimize abrasion (low-friction principle). Furthermore a coating of the particular sliding partners with appropriate materials is also planned. Favored materials are: titanium, titanium alloys, titanium carbide, alloys of cobalt and chrome or other appropriate metals, tantalum or appropriate tantalum alloys, suitable ceramic materials as well as suitable plastics or compound materials.

In a favored design of a three-part prosthesis, as per the invention, it is intended, that the radii of curvature of the convexities of upper and lower side of the middle sliding partner as well as the corresponding concavities of the upper and lower sliding partners are identical. In the case of identically curved convexities on upper and lower side it is, dependent on the design, furthermore intended, that the maximal heights of the convexities of the middle sliding partner on the upper and lower side are to a same or different extent less than in case of a common axis of rotation of a segment of a circle according to point 2 a) a. and, in case of a present edge, the height of the edge is reduced by the same amount as the height of the convexities or the height of the edge remains unchanged or is differently changed than the height of the convexities, with the maximal height of the convexities on the upper and lower side being equal or different.

By these measures, as per the invention, the total height of the prosthesis is reduced, because the middle sliding partner is flattened. At the same time the articulating areas are increased in size, resulting in a gentle (w.r.t. the material) load transfer within the intervertebral space. By this design dimensions of the prosthesis are thus reached, which make it possible to implant it in physiologically especially small intervertebral spaces. Additionally such a design enables the variability of the height of the middle sliding partner and thus the possibility of adapting a prosthesis to the required height.

Furthermore designs are intended where the radii of curvature of the convexities of upper and lower side of the middle sliding partner as well as the corresponding concavities of the upper and lower sliding partners are different. As a result the possibilities to adapt the degree of motion of an intervertebral disc prosthesis, as per the invention, to the physiological degree of motion are expanded. Even at different radii of curvature of the convexities on the upper and lower side of a middle sliding partner a design is intended, where the maximal height of the convexities of the middle sliding partner is equally or differently lower on the upper and lower side than in axes of rotation according to point 2 a) a. of two differently curved segments of a circle and/or in the case of an edge the height of the edge is reduced by the same amount as the height of the convexity(ies) or the height of the edge remains the same or is different from the change of height of the convexity(ies), with the maximal heights of the convexities on the upper and lower side of the middle sliding partner thereby being equal or different.

A slip out of the middle sliding partner from this "compact" design of a three part intervertebral disc prosthesis, as per the invention, is prevented by the motion adapted heights of the convexities on the upper and lower side and the corresponding concavities starting with the edge around the articulation areas and by the closed gap between the edges of the sliding partners at terminal inclination. The convexities are designed in such a way that they will interdigitate deeply enough into the articulating concavities. A sufficient opening of the whole prosthesis post-operatively, which is a prerequisite for a slip out of the middle sliding partner, is thus not possible.

For a two- or three-part intervertebral disc prosthesis, as per the invention, a maximal aperture angle of 6°-10° including, for example 6°-7°, 6°-8°, 6°-9°, 7°-8°, 7°-9°, 7°-10°, 8°-9° or 8°-10° during one-sided gap closure of the sliding partners during extension or flexion, and of 3°-6° including, for example 4°-6°, 5°-6°, 3°-4°, 3°-5° or 4°-5° during one-sided lateral gap-closure is intended. The concrete maximal motions can be constructively adapted for the lumbar and cervical spine, without the need of an "individual prosthesis" for every single intervertebral disc. The aperture angles correspond to the natural segment mobility and are reached by suitable choices of convexity(ies) and concavity(ies) in connection with the design of the surrounding edges (see above). To compensate for tolerances within the motion segment, an additional 3° will be included for every direction of motion.

In both a functional two-part and functional three-part prosthesis the rotation of the sliding partners around a fictitious central vertical axis is stopped at congruency of the convexity(ies) and concavity(ies) between the articulating sliding partners.

In a further design of a two- or three-part intervertebral disc prosthesis it is intended, that the concavity is formed laterally broader than the corresponding convexity. The concave recess is laterally broadened, and the broadening is rounded-off. This rounded-off shape complies with the shape of the convexity. The shape can also be a concave section of a torus, which laterolaterally has the same radius of curvature as the convexity has laterolateral. By this design, as per the invention, a limited rotation is enabled, which, depending on the degree of the lateral broadening, allows a rotation to each side around a fictitious vertical axis of up to 3 degrees including up to about 2 degrees and up to about 1 degree for the lumbar spine and up to 6 degrees including up to about 5 degrees, up to about 4 degrees, up to about 3 degrees, up to about 2 degrees and up to about 1 degree for the cervical spine. To compensate for tolerances within the motion segment an additional 2 degrees, including for example about one degree, to each side is included.

In the case a concavity is laterally broader than the articulating convexity the convexity can turn within the concave recess along a diagonal. Depending on the embodiment of the lateral broadening, a limited rotation of the sliding partners against each other can be achieved without a change of the total height of the prosthesis. In any case, the rotation of the convexity is, however, limited by the resistance, which results from the motion of the convexity of the prosthesis onto the margin of the articulation area of the concavity.

In an alternative design of the concavity of an intervertebral disc prosthesis, as per the invention, it is intended that the concavity that corresponds to the convexity is built as a hollow ball-shaped recess, and where the radius of curvature corresponds to the bigger radius of curvature of the corresponding convexity.

Theoretically, in such articulation partners an unlimited rotation of the sliding partners—in a three-part prosthesis of the middle sliding partner—is feasible. That is why such a design is particularly intended for two-part prostheses, because an unlimited rotation of a middle sliding partner is impossible, by virtue of its assembly, to an upper or lower vertebral body.

In a further preferred design of a two- or three-part intervertebral disc prostheses, as per the invention, a shift of up to 4 mm including up to about 3 mm, about 2 mm or about 1 mm away from a midline sagittal section to dorsal of the convexity(ies) and corresponding concavity(ies) is intended.

A dorsally displaced center of rotation particularly corresponds, above all, to the physiological situation between the lumbar spine and the sacral bone and at same time the differences between the possible inclination angles in extension and flexion are achieved.

It is furthermore intended that the edges of the sliding partners end outwardly rectangular, otherwise angular, curved or combined straight, curved and/or angular. Especially for a three-part prosthesis an embodiment of prosthesis with middle sliding partner with a edge is conceivable, in which upper and lower side of the middle sliding partner end rectangularly or curved in the outer edge regions and the breadth of the edge is designed equally or differently than the upper and lower sliding partner. Thus the middle sliding partner remains between the upper and lower sliding partner during terminal inclination because during gap-closure, the concavity of the upper and/or lower sliding partner covers the corresponding respective convexity of the middle sliding partner beyond its maximal height.

In a further design of a three part intervertebral disc prosthesis it is intended that the height of the middle sliding partner partly or totally continuously increases beginning from the transition area between the convexity and the edge up unto the peripheral edge area. This is intended without the size of the aperture angle changing as a result of an adaptation to the height of the edge of the upper and lower sliding partners. This "dovetail" shape of the edge of the middle sliding partner increases its safety against a dislocation.

As per the invention, a shape for the upper and lower sliding partner is intended for three part-prosthesis, in which the peripheral edge areas are complete or partly hook-shaped, perpendicular, otherwise angular, curved or a combination thereof in direction of the other outer sliding partner. In this design, the edge of the middle sliding partner is narrower there, so that the middle sliding partner is partly or completely covered by the feature of one or both outer sliding partners, in order to prevent a slip-out of the middle sliding device. Advantageously, the edge of the middle sliding partner is adapted in such a way to the shape of the edge of the outer sliding partners, that during terminal gap-closure as high as possible an area of the articulating sliding partners comes into contact.

Furthermore it is intended as per the invention, to provide a three-part prosthesis, in which there is as an additional safeguard for the middle sliding partner with an edge, a stop against a slip-out, slip-away or slip-aside (luxation) out of the prosthesis during a gap-closure. This is part of the outer edge of the middle sliding partner. The stop of the middle sliding partner is located next to the periphery of the upper and/or lower sliding partner and it is higher at least on the upper or the lower side than the edge of the middle sliding partner.

This stop, as an additional safeguard against a slip-out, slip-away or slip-aside (luxation) out of the prosthesis, as per the invention, also is designed in such a way that it is a part of the edge of the middle sliding core. It is higher than the edge of the middle sliding partner at the upper or lower side and is led within a groove in the edge of the upper and/or the lower sliding partner with the necessary tolerance for the maximal sliding motion of the sliding partners.

As per the invention, a stop is an outwardly directed extension of the edge of a middle sliding partner, which as result of its design, is suited to prevent a slip-out of the middle sliding partner out of the concavities of the upper and lower sliding partner. It is not necessary that it encloses the middle sliding partner completely, because this could result in a limitation of the maximal mobility of all sliding partners. Where required, it is rather arranged in definite distances or opposite of positions of the edge, which represent possible positions for a slip-out of the middle sliding partner. If the stop is higher on the upper and lower side than the edge of the middle sliding partner, it can for instance be shaped like a drawing-pin, sticking with the tip from outside into the edge, so that the head of the drawing-pin juts out over the upper and lower edge of the middle sliding partner and prevents a slip-out of the middle sliding partner during a terminal inclination in direction of the drawing pin by stopping its movement via contact to the upper and lower sliding partner.

If a stop, as a safeguard to prevent slip-out, is part of the edge of the sliding partners, the height of the convexity depends only—with regard to the anatomy and the material properties—on the desired maximal inclination angles, which is also influenced by this them (see above).

A stop to secure the middle sliding partner of a three-part prosthesis is advantageously shaped in such a way that it is part of the contact areas during gap-closure of the edges of the sliding partners. The stop not only has a securing function, but additionally it increases the load bearing area during terminal inclination of the sliding partners; the advantages of this have been described above. The possibility for such a design, however, depends crucially on the external shape of the upper and lowers sliding partners and the respective breadth of the edge of the convexity and concavity.

Further it is intended for an intervertebral disc prosthesis, as per the invention, that the outer circumferences of the upper and lower sliding partners may taper off from dorsal to ventral (lumbar spine) or from ventral to dorsal (cervical spine) in a transversal view. This tapering off of the outer circumferences of the upper and lower sliding partners may laterally have the shape of identical curves and preferably a segment of a circle. Where necessary, area and shape of the outer circumference of the upper and lower sliding partners can be equal or unequal and thus be adapted to the size of the respective vertebral body with which they are assembled.

The tapering off shape of the upper and lower sliding partners of the prosthetic plates correspond generally speaking to the usable area of a vertebral body in a transversal view resulting in an optimal use of the area at disposal for anchoring the sliding partners with the aim of using a maximized area for load transfer acting on the sliding partners.

Adaptations to the sliding partners, as per the invention, of the intervertebral disc prosthesis are further intended, in which upper and/or lower sliding partners are built in such a way in a frontal and/or sagittal section, that the out- and inside of the upper and/or lower sliding partners are parallel or not parallel to each other. By this measure, as per the invention, an intervertebral disc prosthesis can be adapted to vertebral body endplates, which are not standing parallel in a frontal view or which, in a sagittal view, should build an optimal lordosis and positioning of the sliding areas.

It is further intended, that in a two- and three part design, as per the invention, the convexity (two-part prosthesis) or the middle sliding partner (three part prosthesis) is parallel or non-parallel with respect to a fictitious horizontal. In the case of an non-parallel design, the upper- and lower sides stand in an angle with respect to a fictitious horizontal with the angle being the same above and below or different with a middle sliding partner. The convexity(ies) and corresponding concavity(ies) in the two- and three part prosthesis are symmetrical or asymmetrical in their surface design. By virtue of the angular convexity or the angular middle sliding partner, adaptations to asymmetries of the intervertebral space, into which the prosthesis is to be implanted, are also possible.

For a reliable anchorage of the implants within the intervertebral space, a marginal and/or plane interdigitation of the exterior sides of the upper and lower sliding partners serves for the connection with an upper and lower vertebral body. The exterior sides themselves are flat or convex in shape and it is possible to coat the interdigitation or the vertebra-directed surfaces with or without interdigitation bio-actively or bluntly. To minimize the risk of a fracture an interdigitation with three ventral and two dorsally arranged anchoring teeth is advantageous. As an alternative laterally continuously arranged rows of teeth are favoured for an improved guidance of the upper and lower sliding partners during implantation between the vertebral bodies, because the forceps of the surgeon can grip in the middle gap between the rows of teeth or into holes of the upper and lower sliding partners at the level with the teeth.

To facilitate implantation or explantation of the intervertebral disc prosthesis, the upper and/or lower sliding partners are furbished with provisions for instruments in a further design. These provisions preferably comprise holes or moulds which the required instrument of the surgeon can grip so that a secure fixation of the respective sliding partner is possible.

Furthermore as absolute measurements for an intervertebral disc prosthesis, as per the invention, a maximal width (frontal view) of 14 to 48 mm, including about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, about 42 mm, about 44 mm or about 46 mm, a maximal depth (sagittal view) of 11 to 35 mm, including about 13, about 15 mm, about 17 mm, about 19 mm, about 21 mm, about 23 mm, about 25 mm, about 27 mm, about 29 mm, about 31 mm, about 33 mm, and a maximal height of 4 to 18 mm, including about 6 mm, about 8 mm, about 10 mm, about 12 mm, about 14 mm or about 16 mm, are intended. These measurements are taken from the natural conditions of the lumbar and cervical spine and assure that the situation with an intervertebral disc prosthesis, as per the invention, comes very close to the in vivo situation.

Further for an intervertebral disc prosthesis as per the invention one or more X-ray contrast providing markers are provided, which are located under the surface of each of the non X-ray contrast providing parts of the prosthesis. That way it is possible to exactly control the position of these parts of the intervertebral disc prosthesis after the implantation. Furthermore it is possible to check, if these parts have changed their position or if they are still in the right position in defined timely intervals.

Further advantageous measures are described in the dependent claims; the invention is described in the following by examples and figures.

DESCRIPTION OF VARIOUS AND PREFERRED EMBODIMENTS OF THE INVENTION

Figure 1A:
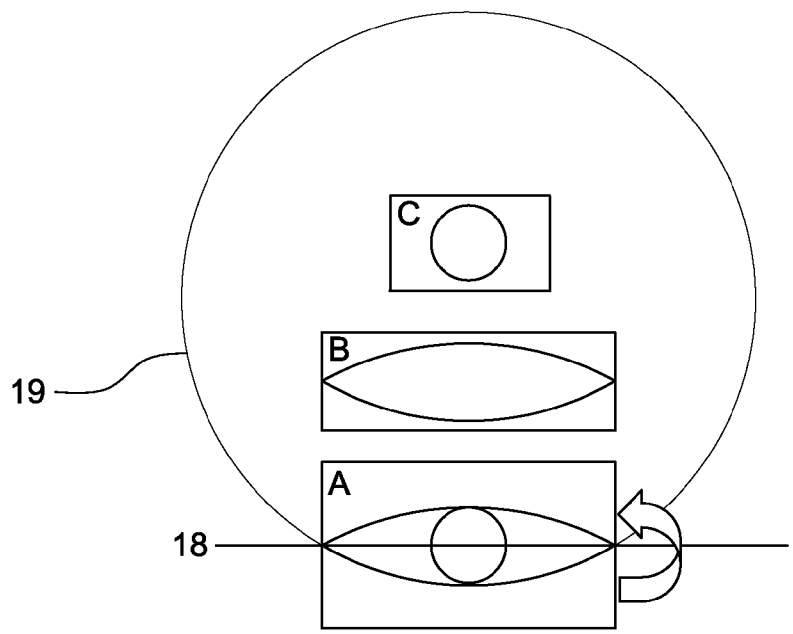
FIG. 1 *a* Schematic view of a middle sliding partner with identically curved upper and lower side, derived from a circumference and a secant as rotation axis:
  A: Correlation between the maximal heights of the convexities in a mediofrontal and median transversal section of the middle sliding partner and the diameter in a median sagittal section,
  B: Convexity of the middle sliding partner without edge in a median frontal and transversal section
  C: Convexity of the middle sliding partner in a median section FIG. 1 *b* Schematic view of a frontal section (left) and sagittal section (right)
Figure 1B:
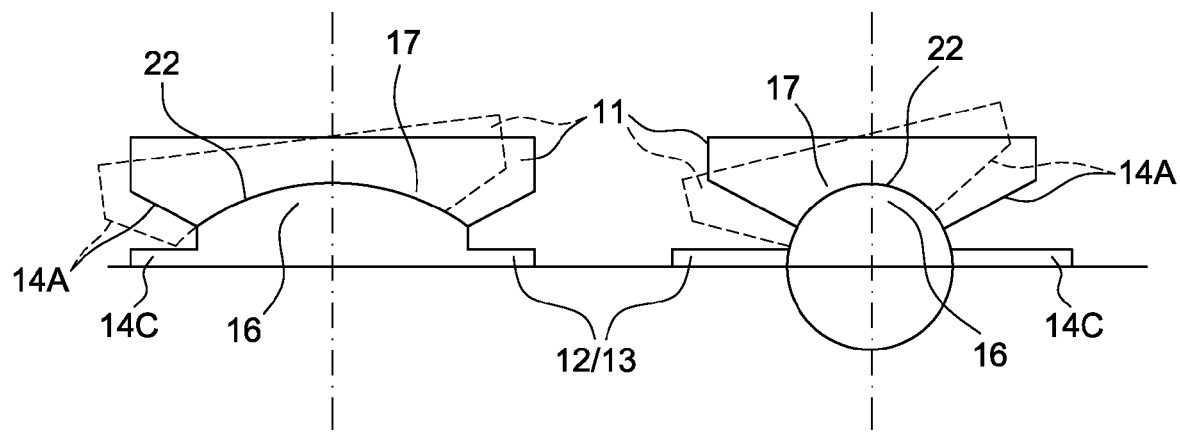

In FIG. 1 a, part A of the figure shows how the curvation of the surfaces of a middle sliding partner with identical upper and lower sides are derived from a circumference 19 and originates from the rotation of the smaller segment of a circle, which is indicated by the arrow, around the secant 18. Part B of the figure shows the shape resulting from the rotation, which is identical in a frontal and transversal section. In a sagittal section C of the solid body, which originates from the rotation of the smaller segment of a circle around the secant 18, it has in each view a circular cross-section. The radii within the sagittal section decrease continuously from the middle of the geometric body to both lateral sides.

In FIG. 1 b, the left schematically depicts a frontal view of a sliding area 22, 23 of an intervertebral two-part or three-part disc prosthesis, as per the invention. The right part of FIG. 1 b schematically shows a sagittal view. The figure illustrates the identical heights of the convexity 16 within the frontal and sagittal view, and the 90 degree shifted radii of curvature differ clearly from each other. The broken line represents a maximally inclined upper sliding partner 11 with concavity 17, articulating with the convexity 16 of a middle sliding partner 13 of a three-part intervertebral disc prosthesis or the lower sliding partner of a two-part prosthesis 12. For an exact depiction of the angular correlations around the convexity 16, the edge 14C surrounding the convexity 16 always has the same height. As can be seen from both views of FIG. 1 b, the transition area of the concavity 17 to the surfaces of the edge 14A is the part of the prosthesis limiting the mobility of the sliding partner 11, 12, 13 to each other, because this part of the prosthesis comes into contact first without the edge 14A in this schematic view having closed gaps at terminal inclination. A smaller mobility of the sliding partners 11, 12, 13 can be observed in the frontal section compared to the sagittal section, resulting from the different radii of curvatures. Consequently a convexity 16 and a concavity 17 designed as per the invention allow a greater inclination in the dorsoventral direction of the sliding partners 11, 12, 13 than in laterolateral direction.

In order to come into contact with each other, the areas of the edges 14A and C have to be inclined towards each other. For this, dorsally and ventrally, edges 14A and C have to have a greater aperture angle for gap closure than the lateral edges 14A and C. The respective inclination of the edges 14A and C serves for the purpose of closing the gap. By itself, it has no influence on the maximal mobility of the sliding partners 11, 12, 13 towards each other. As far as the inclination of the edge of the middle sliding partner continuously increases the height of its edge towards the periphery, it stabilizes the middle sliding partner from a dislocation during terminal motions of the three sliding partners. The different inclinations of the edges 14A and C have a flowing transition. An intervertebral disc prosthesis, as per the invention, does not necessarily provide an edge 14C for the middle sliding partner 13. If a middle sliding partner 13 has no edge 14C, the upper and lower sliding partners 11, 12 preferably have edges 14A and B (14B is not shown) with inclinations enabling a maximal closure of the gaps between them during terminal inclination. The convexities 16 of a middle sliding partner and the concavities 17 of the upper and lower sliding partners 11, 12, so far a middle sliding partner 13, having no edge 14C, are preferably designed in such a way in that the convexities 16 interdigitate deeply enough into the concavities 17, to prevent a slip-out of the middle sliding partner 13 on the one hand, and to allow contact between the edges 14 with each other on the other hand.

Figures 2A, 2B:
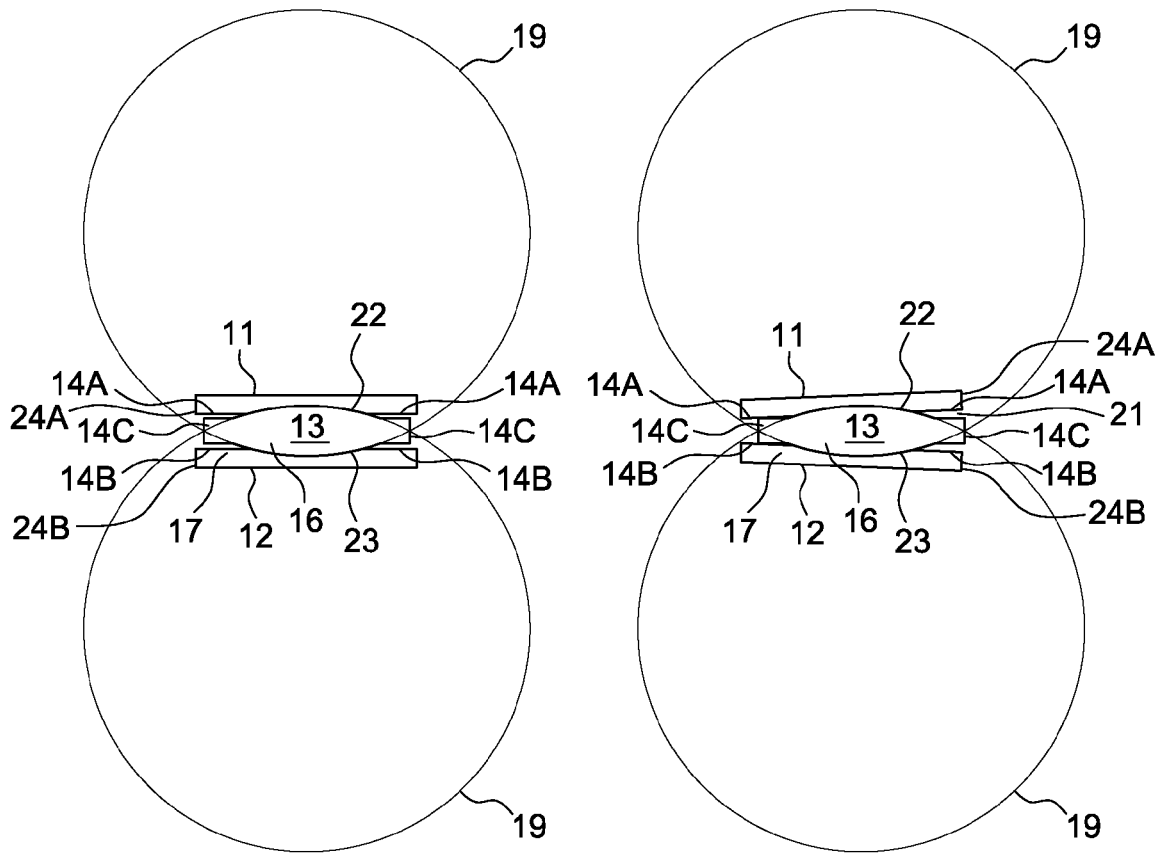
FIG. 2 Schematic frontal view of a three part intervertebral disc prosthesis, as per the invention, with edge of the middle sliding partner, derived from identical circumflexes:
  a: without inclination of the sliding partners
  b: terminal inclination of the sliding partners to the left FIG. 3 *a-c* Schematic sagittal view of a three-part intervertebral disc prosthesis according to the invention with edge of the middle sliding partner a: without inclination of the sliding partners
b: terminal inclination of the sliding partners to the left
c: with flattened middle sliding partner FIG. 4 a-d Schematic view of a two-part intervertebral disc prosthesis, as per the invention. On the left each prosthesis is depicted without inclination and on the right with terminal inclined and closed gap of the sliding partners:
a: frontal view
b: sagittal view
c: transversal view with concavity
d: transversal view with laterally broadened concavity and with convexity, left without, right with rotation FIG. 5 a-g Schematic view of a three-part intervertebral disc prosthesis, as per the invention, with edge of the middle sliding partner. In the frontal and sagittal view on the left each prosthesis is depicted without inclination and on the right with terminal inclined and closed gap:
a: frontal view
b: sagittal view
c: transversal view with concavity
d: transversal view with laterally broadened concavity and with convexity, left without, right with rotation
e: transversal view with dorsally displaced rotation center of the concavity (for the lumbar spine)
f: sagittal view with dorsally displaced rotation center (for the lumbar spine)
g: transversal view with laterally broadened concavity, with convexity and dorsally displaced rotation center (for the lumbar spine), left without, right with rotation of the convexity within the concavity FIG. 6 a-e Schematic view of different shapes of an upper and lower sliding partners for the lumbar spine FIG. 7 a, b Schematic view of the arrangement of teeth on the outside of upper and lower sliding partners for the lumbar spine FIG. 8 Schematic view of the middle sliding partner of the intervertebral disc prosthesis, as per the invention, (above as FIG. 1a, below middle sliding partner with frontal and sagittal equal heights, however sagitally greater articulation area, due to horizontally reduced symmetrical fragment of an initially larger sliding partner)

FIG. 2 a and b each show a schematic frontal view of a three-part intervertebral disc prosthesis as per the invention, with the edge of the middle sliding partner 13, derived from identical circumferences 19. In FIG. 2a the prosthesis is shown in a so-called "zero position," in which the upper and lower as well as the middle sliding partner 11, 12, 13 are not inclined towards each other. In FIG. 2 b a terminal inclination of all three sliding partners 11, 12, 13 is depicted with a gap-closure on the left side of the prosthesis.

The radii of curvature of the middle sliding partner 13 are identical on the upper and lower side. They form an upper and a lower articulation area 22, 23 respectively with the corresponding concavities of the upper and lower sliding partner 11, 12. The convexity 16 of the middle sliding partner 13 is totally enclosed by the edge 14C of the convexity 16. The corresponding concavity 17 is also totally surrounded by an edge 14A and B, respectively.

At a terminal gap closure on one side (right part) the aperture angle 21 increases corresponding to the gap closing on the opposite side of the convexity/concavity 16, 17.

Figure 3A:
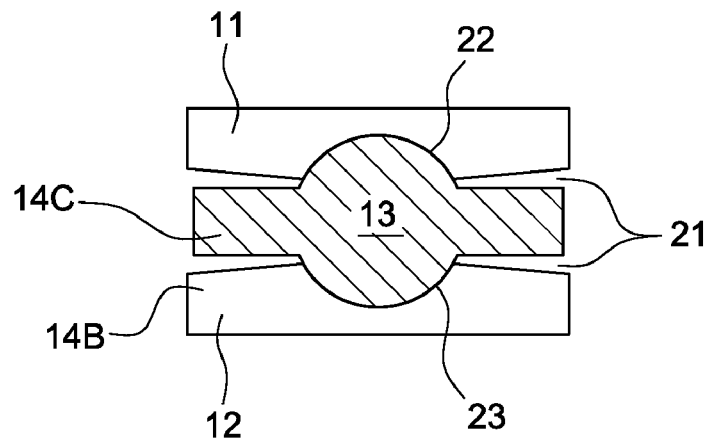
Figure 3B:
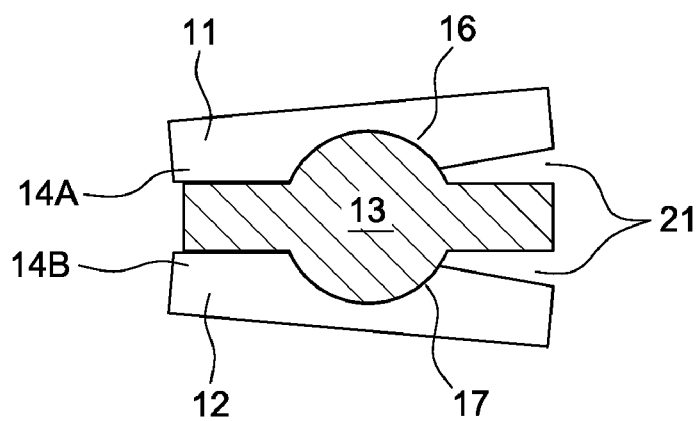
Figure 3C:
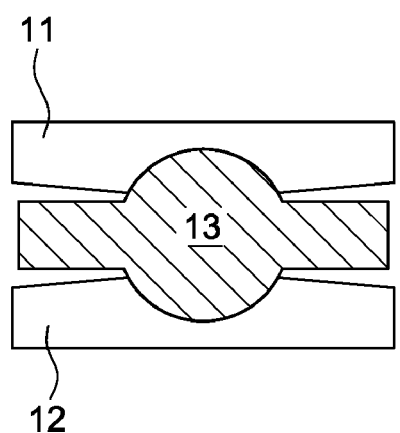

The FIGS. 3 a-c show a schematic sagittal view of a three-part intervertebral disc prosthesis, as per the invention, with an edge 14C of the middle sliding partner 13. The upper sliding partner 11, the lower sliding partner 12 and the in-between localized sliding partner 13 can be seen. In FIG. 3 a and b, the circumferences of the upper convexity and the lower convexity are part of the same circle, in FIG. 3 c the convexity is flattened on upper and lower side. In FIG. 3, the prosthesis is again shown in "zero position," with a dorsal or a ventral gap closure shown in FIG. 3 b. In FIG. 3 b the aperture angle 21 has correspondingly increased as the gap has closed on the opposite side of the concave-convex part of the sliding areas 22, 23. A gap-closure results between the edges 14A, B and C at terminal inclination of all sliding partners 11, 12, 13, so that an optimal distribution of the pressure is guaranteed.

FIG. 4 a-d show a schematic view of a two-part intervertebral disc prosthesis, as per the invention. On the left the prosthesis is always shown without inclination and on the right with terminal gap-closure of the sliding partners 11, 12.

Figure 4A:
Figure 4B:
Figure 4C:
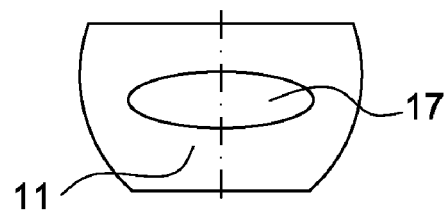
Figure 4D:
Figure 6A:
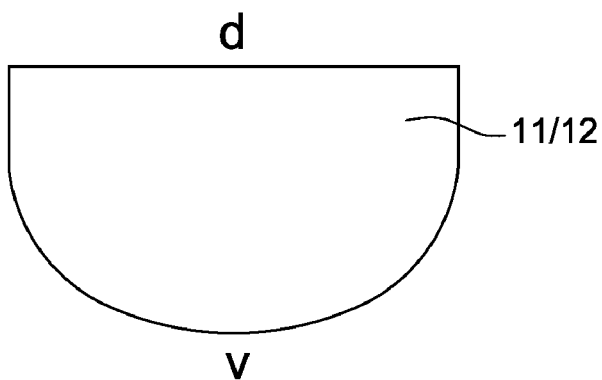
Figure 6D:
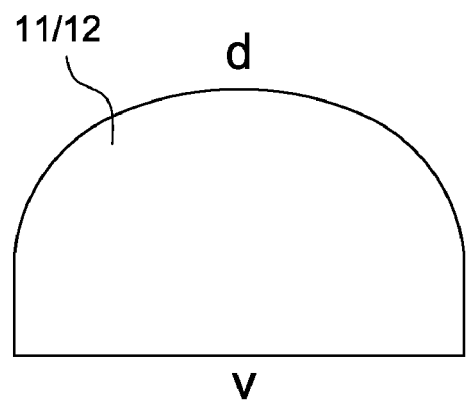
Figure 6B:
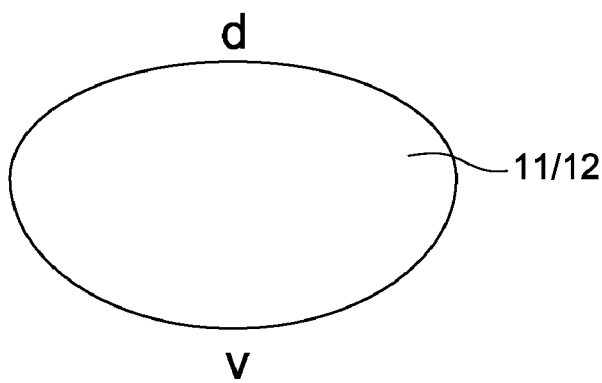
Figure 6C:
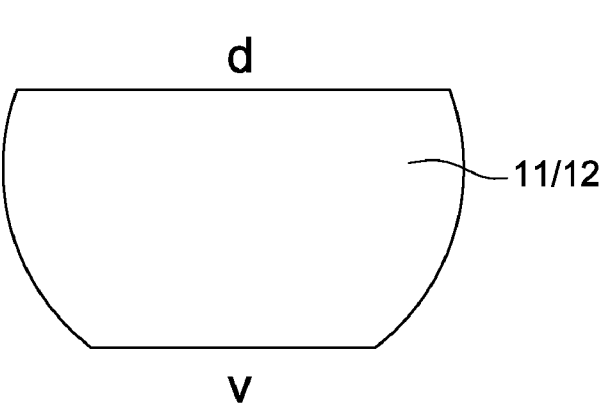
Figure 6E:
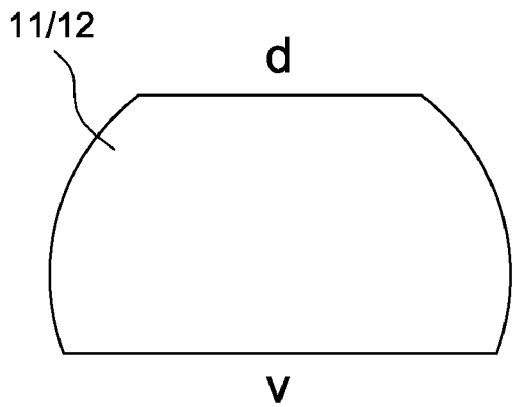

FIG. 4a shows a median frontal section and FIG. 4 b a median sagittal section across the prosthesis, as per the invention. The lower sliding partner 12 can comprise two different materials, depending on the chosen design; this is indicated by the colors grey and black. The part with the convexity (hatched) comprises a different material than the part of the sliding partner 12 directed toward the vertebral body (bottom). Preferred are upper sliding partner 11 and lower sliding partner 12 (part at bottom) of the same material. In a special version only the convexity 16 comprises a different material.

FIG. 4 c shows a top view onto the inner side of an upper sliding partner 11 of a two-part intervertebral prosthesis. The concave recess 17, having a shape corresponding to the convexity 16 (FIG. 4d) of the lower sliding partner 12 is indicated. In FIG. 4 d a top view is also depicted onto the inner side of an upper sliding partner 11 with concave recess 17 as well as convexity 16 of the lower sliding partner 17 of a two-part intervertebral disc prosthesis. The concave recess 17 is laterally broadened, with the broadening being rounded off and the shape being orientated at the shape of the convexity 16. By virtue of the lateral broadening, a minimal rotation of the convexity 16 is enabled; this is indicated in the right part of FIG. 4d.

FIG. 5 shows a schematic view of a three-part intervertebral disc prosthesis, as per the invention, with the edge of the middle sliding partner 13. In the frontal and sagittal views the prosthesis is always depicted without inclination and on the right side with terminally closed gap between the sliding partners.

In FIG. 5a a median frontal view of the prosthesis is shown, with upper sliding partner 11, lower sliding partner 12 and middle sliding partner 13. Such a section has already been extensively described for FIG. 2. Preferably both sliding partners 11, 12 comprise the same material or they are identically coated. It is not necessary, but preferred, that the middle sliding partner 13 comprises a different material than the upper and lower sliding partners 11, 12, or it has been coated equally or differently. Material and coatings are preferably chosen in a way that the abrasion of the sliding partners is minimized (low-friction-principle).

In FIG. 5 b a three-part prosthesis in a central sagittal view is shown. For a detailed description refer to FIGS. 3 a-c, where a sagittal view of a three-part prosthesis with upper sliding partner 11, lower sliding partner 12 and middle sliding partner 13 is also depicted, without inclination of the sliding partners 11, 12, 13 to each other as well as with terminal dorsal or ventral inclination. This view is depicted here for the purpose completeness.

FIG. 5 c shows a transversal view of upper and lower sliding partners 11, 12 of a three-part intervertebral disc prosthesis with concavity 17, which is correspondingly shaped to the convexity on the upper and lower side of the middle sliding partner 13.

FIG. 5 d shows a transversal view of an upper and lower sliding partner 11, 12 with laterally broadened concavity 17, in which a convexity 16, formed as per the invention, is embedded (5d left). Because of the lateral broadening of the concavity 17, it is possible for the convexity 16 to slightly rotate within the laterally broadened recess (5d right).

FIGS. 5 e-g show views of a three-part prosthesis depicted like FIGS. 5 b-d, with the center of rotation of these prostheses (for the lumbar spine) dorsally displaced.

The FIGS. 6a-e each show a top view onto alternative designs of the circumference of upper and lower sliding partner 11, 12. The small letters indicate the orientation with respect to the dorsoventral alignment of the plates for the lumbar spine (d=dorsal; v=ventral), which is however reversed for the cervical spine (v=dorsal; d=ventral).

Figure 7A:
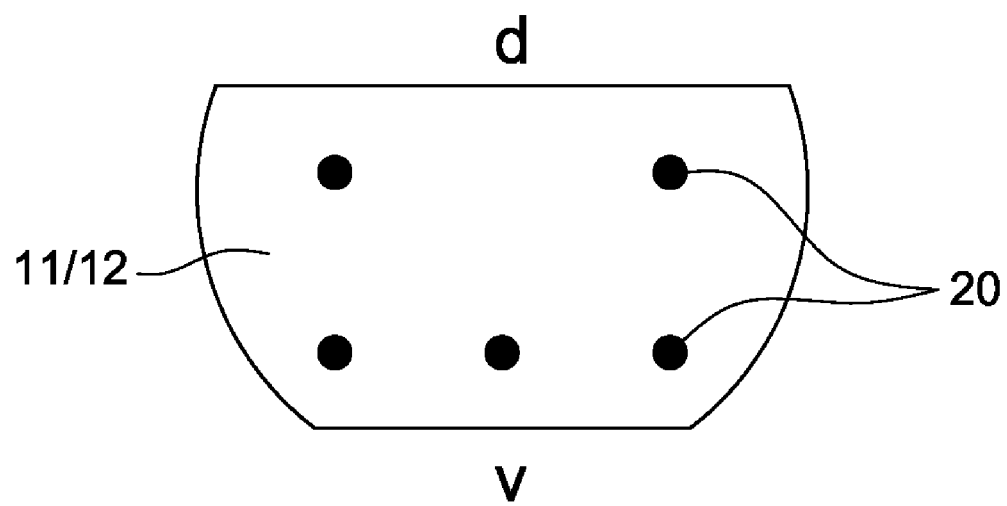
Figure 7B:
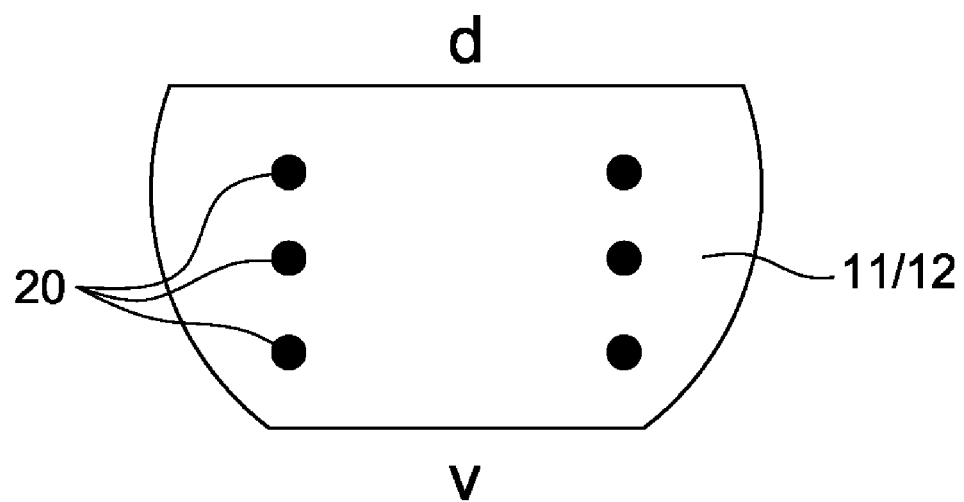

The FIGS. 7 a and b show alternative arrangements of the anchoring teeth 20 on the outside of the upper and lower sliding partners 11, 12. Again the orientation of the sliding partners with respect to the dorsoventral orientation is indicated by the small letters (d=dorsal; v=ventral). Dorsally in the middle no anchoring teeth 20 are intended, because this results on one hand in sparing the vertebral bodies and on the other hand facilitates the implantation. For the cervical spine the reversed orientation is also without middle dorsal anchoring teeth 20.

Figure 8:
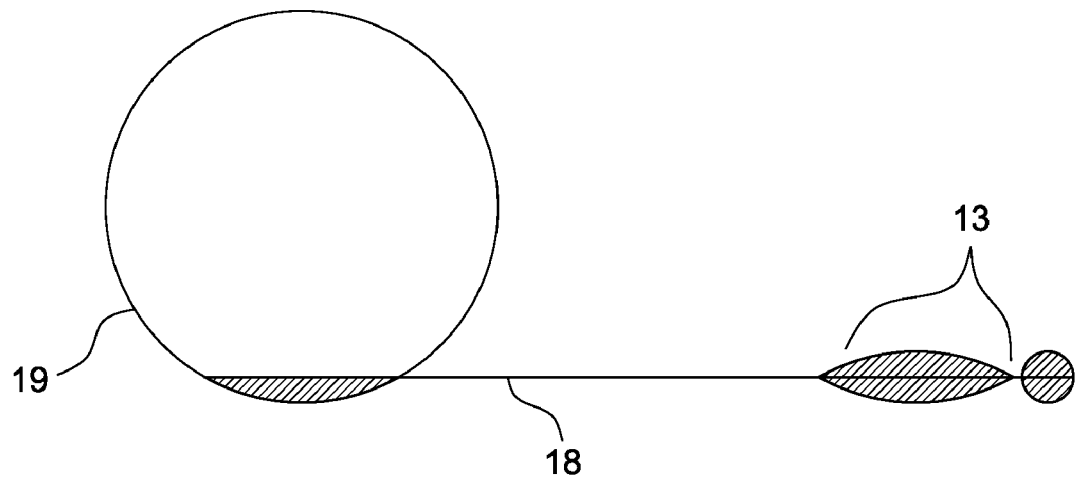
Figure 8:
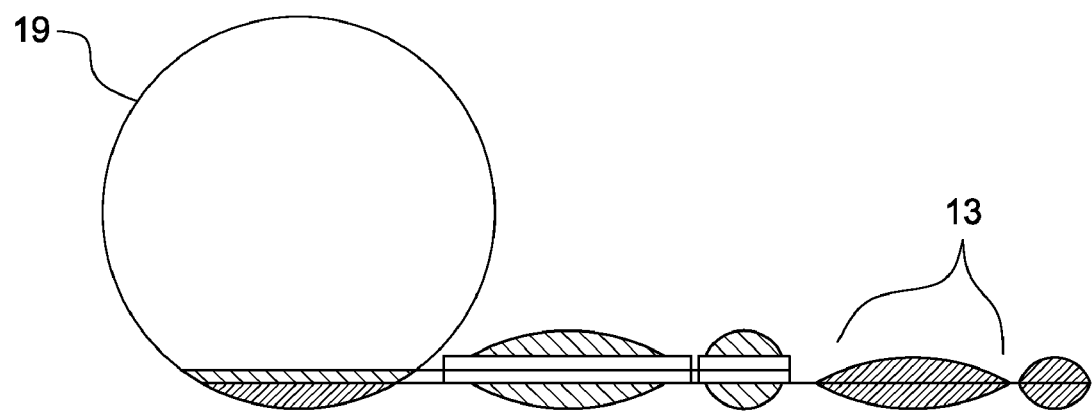

FIG. 8 shows cross-sections through a middle sliding partner 13 without edge and the derivation of the radii of curvature out of the circumference of a circle 19. In the upper part of the illustration, the convexities have a common axis of rotation, which is a secant 18. In the sagittal view such a middle sliding partner 13 has a circular cross section (top right). In the lower part of the illustration, a flattened middle sliding partner 13 is depicted. Here, indicated by a white beam (bottom middle), a symmetrical part is missing in the middle of the frontal view. In such a middle sliding partner 13, derived from a circumference of a circle 19, the sagittal view shows more of a lentiform shape (bottom right). In the frontal view this shape of the flattened middle sliding partner 13 is, however, unchanged compared to the middle sliding partner 13, which is depicted in the upper part of the illustration.

Figure 9A:
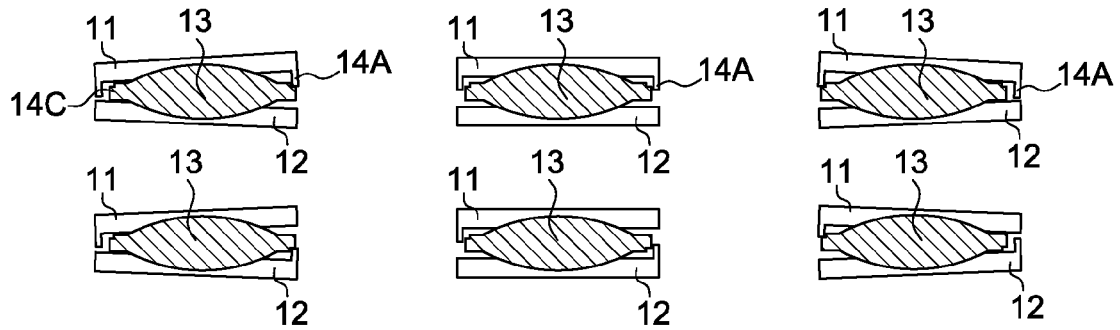
FIG. 9 a-c Schematic view of variations of an intervertebral disc prosthesis as per the invention, with a edge for the safeguard of the middle sliding partner by means of the design of edges of the upper and lower sliding partner. To the left and right the inclination of the prosthesis with the terminal gap-closure of the sliding partners
a: frontal view
b-c: sagittal views FIG. 10 a, b Schematic sagittal view of:
a: middle sliding partner with a stop at its edge
b: assembled three-part intervertebral disc prosthesis according to with edge of the middle sliding partner having a stop and a respective groove FIG. 11 Schematic sagittal view of a three-part intervertebral disc prosthesis with edge of the middle sliding partner indicating permanently and firmly, but reversibly attached parts.
Figure 9B:
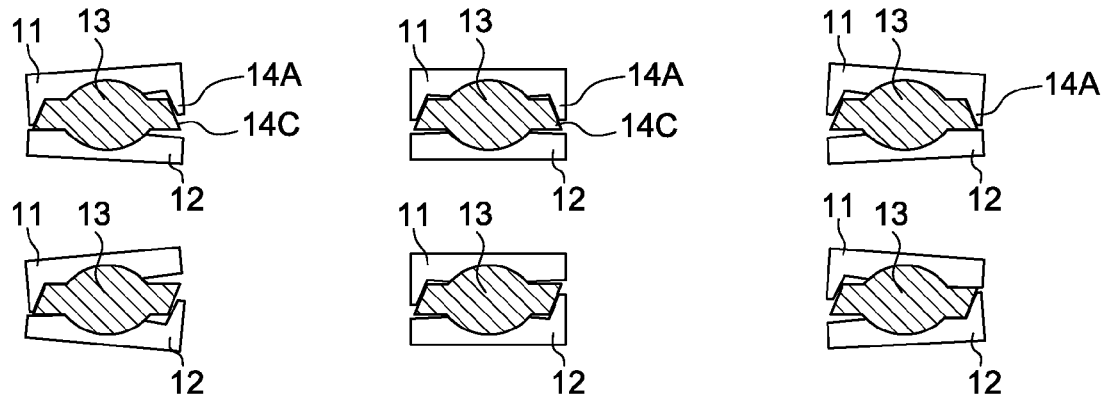
Figure 9C:
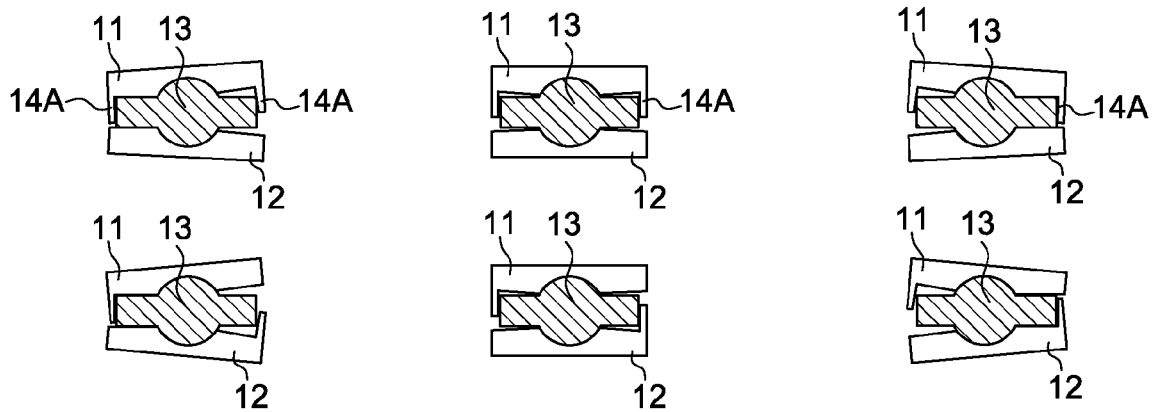
Figure 10A:
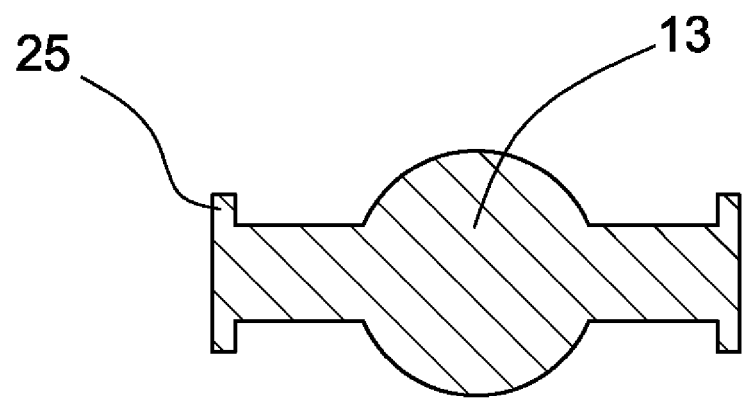
Figure 10B:
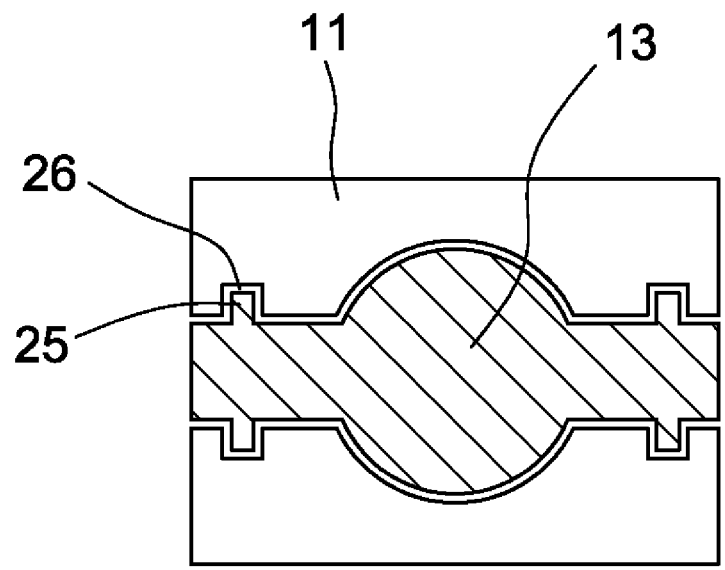
Figure 11:
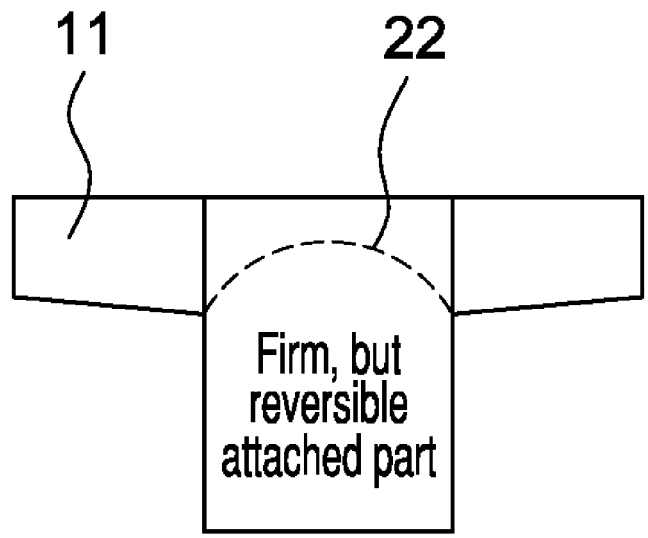
Figure 11:
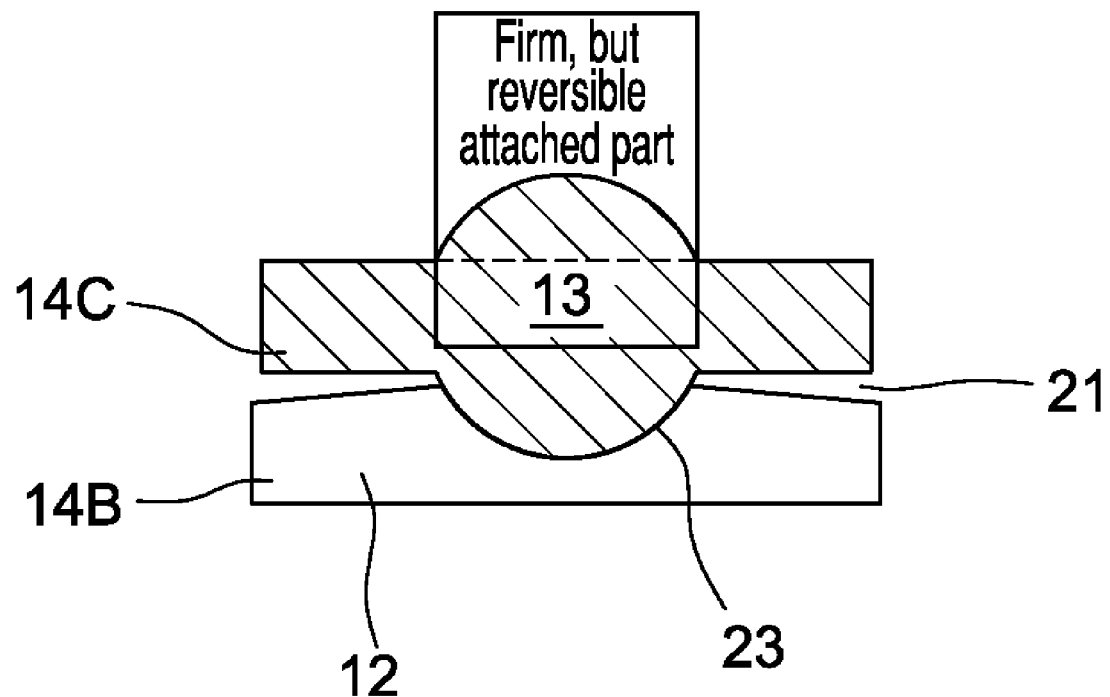

FIGS. 9 a-c show variations of a three part intervertebral disc prosthesis, as per the invention, with an angled edge 14A and B of the upper and/or lower sliding partners 11, 12, respectively, for the purpose of securing the middle sliding partner 13 against a slip out from the prosthesis. By virtue of this design of the upper sliding partner, 11, 12, as per the invention, the middle sliding partner 13 is partly or completely enclosed, because its edge 14C is shorter than the edges 14A and B of the upper and lower sliding partners 11, 12.

The designs depicted in the illustrations of the intervertebral disc prostheses, as per the invention, for a two part as well as a three part design are exemplary and not final. Once given the above disclosure, many other features, modifications, and improvements will become apparent to the skilled artisan. Such other features, modifications, and improvements are therefore considered to be part of this invention.

| Reference Numbers | |
|---|---|
| 11 | upper sliding partner |
| 12 | lower sliding partner |
| 13 | middle sliding partner |
| 14 | edge |
| 14A/B | edge of 11/12, respectively |
| 14C | edge of 13 |
| 16 | convexity |
| 17 | concavity |
| 18 | secant |
| 19 | circumference |
| 20 | anchoring teeth |
| 21 | aperture angle |
| 22 | upper articulation area |
| 23 | lower articulation area |
| 24 | outer rim |
| 24A/B | outer rim of 14A/B, respectively |
| 25 | stop |
| 26 | groove |

The invention claimed is:

1. Intervertebral disc prosthesis for total replacement of an intervertebral disc of a lumbar and cervical spine, comprising an upper sliding partner adapted to firmly assembles to an upper vertebral body, a lower sliding partner adapted to firmly assembles to a lower vertebral body, and located between the upper and lower sliding partner, a middle sliding partner, wherein said sliding partners articulate with each other via an upper sliding area between the middle and upper sliding partners and a lower sliding area between the middle and lower sliding partners, wherein
   a) the middle sliding partner has an upper and lower surface each having a convexity wherein a radius of curvature for each of the convexities:
      a. in the fontal and transversal view of each of the convexities is identical and results from rotation around a secant of a segment of a first circle, wherein the segment corresponds to an entirety of either the convexity of the lower surface or the upper surface, wherein the segment has a height and the height is less than the radius of the first circle and
      b. corresponds in a sagittal view of each of the convexities to the radius of curvature of a second circle, wherein the radius of the second circle corresponds to the height of the segment of the first circle, wherein the diameter of the middle sliding partner is equal to the distance between the apexes of the convexities of the lower surface and upper surface, and
   b) the upper and lower sliding partner have insides with concavities each defined by a corresponding recess to the convexity of the upper and lower surface of the middle sliding partner, each of these concavities being enclosed by a surrounding edge, and
   c) the surrounding edges of the upper and lower sliding partners, which extend between an outer rim and the convexity/concavity define, upon assembly, an outwardly opening aperture angle, with
      a. the aperture angles differing in a central frontal section compared to a central sagittal section due to different inclinations of the edges of the upper and lower sliding partners, to allow a maximal possible area of contact of the edges during terminal motion of the upper and lower sliding partners, and
      b. the different inclinations of the edges of the upper and lower sliding partners seamlessly transiting,
         wherein, at equal aperture angles in a vertical section, on both sides of the upper and lower sliding areas an inclination of the edges is equal or different and
   d) a motion angle is greater in a dorsoventral direction than in a laterolateral direction, resulting from the different radii of curvature defined by the first and second circle, and
   e) a maximal possible motion of the sliding partners towards each other is determined by
      a. the radius of curvature and height of the convexities of the middle sliding partner, design of the corresponding concavities relative to the edges of the upper and lower sliding partners and shape with respect to the corresponding convexities, and
      b. the surrounding edges of the concavities running angular or horizontally.

2. Intervertebral disc prosthesis according to claim 1, wherein the convexities of the middle sliding partner are enclosed by an edge of equal or different breadth.

3. Intervertebral disc prosthesis according to claim 1, wherein the upper, lower and/or middle sliding partners are built as a single piece.

4. Intervertebral disc prosthesis according to claim 1, wherein at least one of the convexities is permanently or firmly, but reversibly attached to the middle sliding partner and/or at least one of the concavities is permanently or firmly, but reversibly attached to the upper and/or lower sliding partner.

5. Intervertebral disc prosthesis according to claim 4, wherein a tongue and groove assembly, a track and corresponding recess, a snap mechanism, gluing or screwing provides for a permanent or firm, but reversible assembly.

6. Intervertebral disc prosthesis according to claim 1 or 2, wherein the upper and lower sliding partner comprise the same material or are equally coated and the middle sliding partner is made of a different material or is differently coated or all sliding partners comprise the same material or are equally coated.

7. Intervertebral disc prosthesis according to claim 1, wherein the radii of curvature of the convexities defined by said first and second circle of the upper and lower surface of the middle sliding partner and the corresponding concavities of the upper and lower sliding partner are identical or different.

8. Intervertebral disc prosthesis according to claim 1, wherein the maximal height of the convexities of the upper and lower surface of the middle sliding partner is less than the radius of said second circle.

9. Intervertebral disc prosthesis according to claim 1 or 2, wherein a maximal aperture angle upon gap-closure via the edges of the upper and lower or the upper, lower and middle sliding partners, respectively, on a side opposite of said maximal aperture angle is, during extension or flexion, between 6 and 10 degrees and during lateral gap-closure between 3 and 6 degrees, with a tolerance of an additional 3 degrees in every direction.

10. Intervertebral disc prosthesis according to claim 1, wherein the congruency between the convexities of the middle sliding partner and the concavities of the upper and lower sliding partner slows down the rotation between the sliding partners around a fictitious central vertical axis.

11. Intervertebral disc prosthesis according to claim 1, wherein at least one concavity is shaped laterally broader than the corresponding convexity, so that a limited rotation motion of the sliding partners with respect to a fictitious central vertical axis is possible, said limited rotation motion being for a cervical spine up to 6 degrees and for a lumbar spine up to 3 degrees to each side, with a tolerance of 2 degrees to each side.

12. Intervertebral disc prosthesis according to claim 1, wherein the concavity of the upper and/or lower sliding partner corresponding with the convexity of the upper and/or lower surface of the middle sliding partner is built as a hollow ball shaped recess, and wherein the radius of curvature of the concavity matches the biggest radius of curvature of the corresponding convexity.

13. Intervertebral disc prosthesis according to claim 1, wherein the convexities and the respective corresponding concavities are dorsally displaced up to 4 mm away from a mediosagittal section.

14. Intervertebral disc prosthesis according to claim 1 or 2, wherein the edges of the upper, lower and/or middle sliding partners are outwardly perpendicular, otherwise angled, curved or a combination of straight, curved, and/or angular.

15. Intervertebral disc prosthesis according to claim 2, wherein as an additional safeguard for the middle sliding partner against slip-out out of the prosthesis during a gap-closure of all three sliding partners, a stop is part of an exterior part of an outer edge of the middle sliding partner, that is located outside the upper and/or lower sliding partner, and wherein the stop on at least its upper or lower side is higher than the edge of the middle sliding partner.

16. Intervertebral disc prosthesis according to claim 2, wherein as an additional safeguard for the middle sliding partner against a slip-out out of the prosthesis during gap-closure of all three sliding partners, a stop is part of the edge of the middle sliding partner, which is higher than the edge of the middle sliding partner and is guided within a groove in an area of the edge of the upper and/or lower sliding partner, wherein a clearance is provided in the groove for maximal sliding motions of the sliding partners.

17. Intervertebral disc prosthesis according to claim 2, wherein as additional safeguarding for the middle sliding partner against a slip-out out of the prosthesis during gap-closure of all three sliding partners, a part or the total of the edge of the middle sliding partner increases continuously in height from a transition area of the convexity to a periphery and the edge of the upper and/or lower sliding partner levels off to the same degree.

18. Intervertebral disc prosthesis according to claim 1 or 2, wherein as an additional safeguard for a middle sliding partner against a slip-out out of the prosthesis during a gap-closure of all three sliding partners, the most outward portions of the edges of the upper and/or lower sliding partner are completely or partially hook-shaped, perpendicular, otherwise angular, curved or a combination thereof in direction of the other one of such upper and/or lower sliding partner.

19. Intervertebral disc prosthesis according to claim 1, wherein surface and shape of an outer circumference of the upper and lower sliding partner are equal or different and can thereby be adapted to the corresponding size of the vertebral body with which they are to be assembled.

20. Intervertebral disc prosthesis according to claim 1, wherein the upper and/or lower sliding partners are designed in such a way that in a frontal and/or sagittal view an outside and inside of the upper and/or lower sliding partner run parallel or non parallel relative to one another.

21. Intervertebral disc prosthesis according to claim 1 or 2, wherein the upper and lower sides of the middle sliding partner are parallel or non parallel with respect to a horizontal, and thus run in a defined angle relative to each other, with the convexities being symmetrical or asymmetrical.

22. Intervertebral disc prosthesis according to claim 1, wherein the upper and lower sliding partner are on their outer surface plane or convex and coated bio-actively.

23. Intervertebral disc prosthesis according to claim 1, wherein the upper and/or lower sliding partner are configured to engage an instrument for implantation or explantation.

24. Intervertebral disc prosthesis according to claim 1, having, upon assembly, a maximal breadth of 14 to 48 mm, a maximal depth of 11 to 35 mm and a maximal height of 4 to 18 mm.

25. Intervertebral disc prosthesis according to claim 1, suitable for implantation into a lumbar spine, and wherein an outer circumference of the upper and lower sliding partners taper off ventrally in the transversal view.

26. Intervertebral disc prosthesis according to claim 1, suitable for implantation into a cervical spine, and wherein the outer circumference of the upper and lower sliding partners tapers off dorsally in the transversal view.

27. Intervertebral disc prosthesis according to claim 25, wherein the tapering off of the outer circumference of the upper and lower sliding partners, has laterally identical curvation or is asymmetric.

28. Intervertebral disc prosthesis according to claim 1 or 2, wherein the intervertebral prosthesis has non X-ray contrast giving parts that are each marked under their surface with one or more radiolucent tags.

29. Intervertebral disc prosthesis according to claim 26, wherein the tapering off of the outer circumference of the upper and lower sliding partners, has laterally identical curvation or is asymmetric.

30. Intervertebral disc prosthesis according to claim 1 or 2, wherein the maximal possible motion of the upper and lower or the upper, lower and middle sliding partners, respectively, toward each other is determined by the height of the concavity relative to its edge.

31. Intervertebral disc prosthesis according to claim 2, wherein the convexities of the middle sliding partner each extend completely across said upper and lower surface, respectively.

32. Intervertebral disc prosthesis according to claim 2, wherein the height of an edge of the middle sliding partner is constant or equally or differently reduced.

33. Intervertebral disc prosthesis according to claim 1, wherein the upper and lower sliding partner are blunt and have, for their primary anchorage with vertebral bodies, rows of anchoring teeth, that are either arranged from dorsal to ventral laterally straight or at an incline or ventral and dorsal in lateral alignment, wherein a respective dorsal row has only laterally arranged anchoring teeth.

* * * * *